United States Patent
Patton et al.

(10) Patent No.: US 11,896,424 B2
(45) Date of Patent: Feb. 13, 2024

(54) AUTOMATED NEEDLE ENTRY DETECTION

(71) Applicant: FUJIFILM Sonosite, Inc., Bothell, WA (US)

(72) Inventors: Edward J. Patton, Bothell, WA (US); Tong Li, Bothell, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 559 days.

(21) Appl. No.: 16/210,253

(22) Filed: Dec. 5, 2018

(65) Prior Publication Data
US 2020/0178927 A1 Jun. 11, 2020

(51) Int. Cl.
*A61B 8/08* (2006.01)
*A61B 8/00* (2006.01)
*A61B 5/00* (2006.01)

(52) U.S. Cl.
CPC .......... *A61B 8/0841* (2013.01); *A61B 5/7267* (2013.01); *A61B 8/463* (2013.01); *A61B 8/54* (2013.01)

(58) Field of Classification Search
CPC ..... A61B 8/0841; A61B 5/7267; A61B 8/463; A61B 8/54; A61B 2017/3413; A61B 8/5246
See application file for complete search history.

(56) References Cited

U.S. PATENT DOCUMENTS

| | | | |
|---|---|---|---|
| 2008/0114240 A1* | 5/2008 | Sasaki | A61B 8/06 600/440 |
| 2011/0021915 A1* | 1/2011 | Feng | A61B 8/08 600/443 |

(Continued)

FOREIGN PATENT DOCUMENTS

| | | |
|---|---|---|
| JP | 2013523343 | 6/2013 |
| JP | 2014138847 | 7/2014 |
| WO | WO 2015/0092582 A1 | 6/2015 |

OTHER PUBLICATIONS

Pourtaherian, A. (2018). Robust needle detection and visualization for 3D ultrasound image-guided interventions. Technische Universiteit Eindhoven (Year: 2018).*

(Continued)

*Primary Examiner* — Bill Thomson
*Assistant Examiner* — Aminah Asghar
(74) *Attorney, Agent, or Firm* — Colby Nipper PLLC

(57) ABSTRACT

In one embodiment, an ultrasound imaging system is configured to receive a set of ultrasound images of a target anatomical region. The set of ultrasound images is combined to create a composite tissue frame. The ultrasound imaging system determines whether an interventional instrument is present within the ultrasound images based on a set of trained classification algorithms based on the set of ultrasound images and the composite tissue frame. If an interventional instrument is detected, the ultrasound imaging system further determines whether an additional ultrasound frame should be captured to image the interventional instrument, and the steer angle to be used for the additional ultrasound image. The ultrasound imaging system determines a linear structure corresponding to the interventional instrument, and creates a blended image showing the interventional instrument and the composite tissue frame.

22 Claims, 9 Drawing Sheets

(56) References Cited

U.S. PATENT DOCUMENTS

| | | | |
|---|---|---|---|
| 2011/0249878 A1* | 10/2011 | Pagoulatos | G06T 5/50 |
| | | | 382/131 |
| 2012/0093397 A1* | 4/2012 | Wang | G06K 9/6257 |
| | | | 382/159 |
| 2013/0289393 A1* | 10/2013 | Kruecker | A61B 8/0841 |
| | | | 600/424 |
| 2014/0187942 A1 | 7/2014 | Wang et al. | |
| 2017/0143295 A1 | 5/2017 | Park et al. | |
| 2017/0281136 A1* | 10/2017 | Mochizuki | A61B 8/14 |
| 2018/0140279 A1* | 5/2018 | Perrey | A61B 8/5223 |
| 2018/0263593 A1* | 9/2018 | Dickie | A61B 8/0841 |
| 2019/0125301 A1* | 5/2019 | Jago | A61B 8/0825 |

OTHER PUBLICATIONS

Hatt et al., "Enhanced needle localization in ultrasound using beam steering and learning-based segmentation," Computerized Medical Imaging and Graphics, vol. 41, pp. 46-54 (2014).

International Search Report and Written Opinion issued in International Application No. PCT/US2019/063675 dated Jun. 24, 2020.

"Foreign Office Action", JP Application No. 2021-532307, dated May 9, 2023, 8 pages.

\* cited by examiner

AUTOMATED NEEDLE ENTRY DETECTION

TECHNICAL FIELD

The disclosed technology relates to ultrasound imaging systems and in particular to ultrasound imaging systems for imaging interventional instruments within a body.

BACKGROUND

Ultrasound imaging is becoming increasingly accepted as the standard of care to be used when guiding an interventional instrument to a desired location within a body. One common use for this procedure is during the application of anesthesia, whereby a physician or a medical technician views an ultrasound image to help guide a needle to a desired nerve or a region of interest. To enhance the ability of the physician to view the needle, many ultrasound systems may incorporate so called "needle visualization" technologies that produce a composite image from an anatomy image of the tissue and an image of the needle. In order to obtain the best image, the transmit beam direction may be nearly perpendicular to a needle or other interventional instrument. In particular embodiments, the user or the ultrasound system may take a number of images at different angles to vary the beam direction, so that the best image of the needle can be determined and used.

In particular embodiments, existing needle detection systems may require the user to provide at least two inputs: 1) indicating that needle detection should be used and 2) the direction from which the needle will enter the image frame (e.g. left or right entry). In particular embodiments, if the user does not indicate that needle detection should be used, no needle detection images may be captured. If the user selects the wrong direction of needle entry, the transmit beam may not intersect with the needle so no needle will be detected. In particular embodiments, another potential issue with existing needle detection systems may be that multiple needle visualization frames must be captured, which may reduce the overall frame rate of the composite images. In particular embodiments, if needle entry information can be determined from the current set of frames, then it may not be necessary to acquire additional needle visualization frames, thereby improving the frame rate of the ultrasound imaging. In particular embodiments, a needle detection system may detect the interventional instrument based on tissue warping or temporal changes in the anatomy image, without relying upon a needle visualization frame to conclude that the interventional instrument is present.

DETAILED DESCRIPTION

As will be explained in further detail below, the disclosed technology relates to improvements in ultrasound imaging systems and in particular to an ultrasound imaging system that is configured to automatically detect the presence of an interventional instrument inserted into the tissue being imaged as well as the direction of entry of the interventional instrument, and produce a combined image of tissue and the interventional instrument. In the description below, the interventional instrument is described as being a needle used to deliver anesthesia or other drugs to a desired location. However, other devices such as biopsy needles, needles for suturing tissue, needles for withdrawing fluids (e.g. amniocentesis), robotic surgical instruments, catheters, guidewires or other invasive medical instruments may also be imaged.

In one embodiment, a processor in the ultrasound system may be configured to cause a number of transmit beams to be created and delivered to a body in order to produce an anatomy image of the tissue under examination. In addition, the processor may be configured to cause a number of transmit beams to be generated at different transmit beam angles, i.e. steer angles, in order to image an interventional instrument. To distinguish the anatomy image from the images of the interventional instrument, the frames of the interventional instrument may be referred to as "needle frames," even if the instrument is not a needle.

Each of the needle frames produced from the transmissions at the different transmit angles may be analyzed to detect the presence of an interventional instrument. In one embodiment, a composite image may be created using the anatomy image and echo data from one or more of the needle frames that are captured using the different transmit beam directions in order to show both the tissue and the position of the interventional instrument. In particular embodiments, by capturing multiple images of the anatomy image and the needle frames over time, it may be possible for the ultrasound imaging system to provide a live feed of composite images to the user, so that the user may observe the position of the interventional instrument in relation to the anatomy over time.

Figure 1:
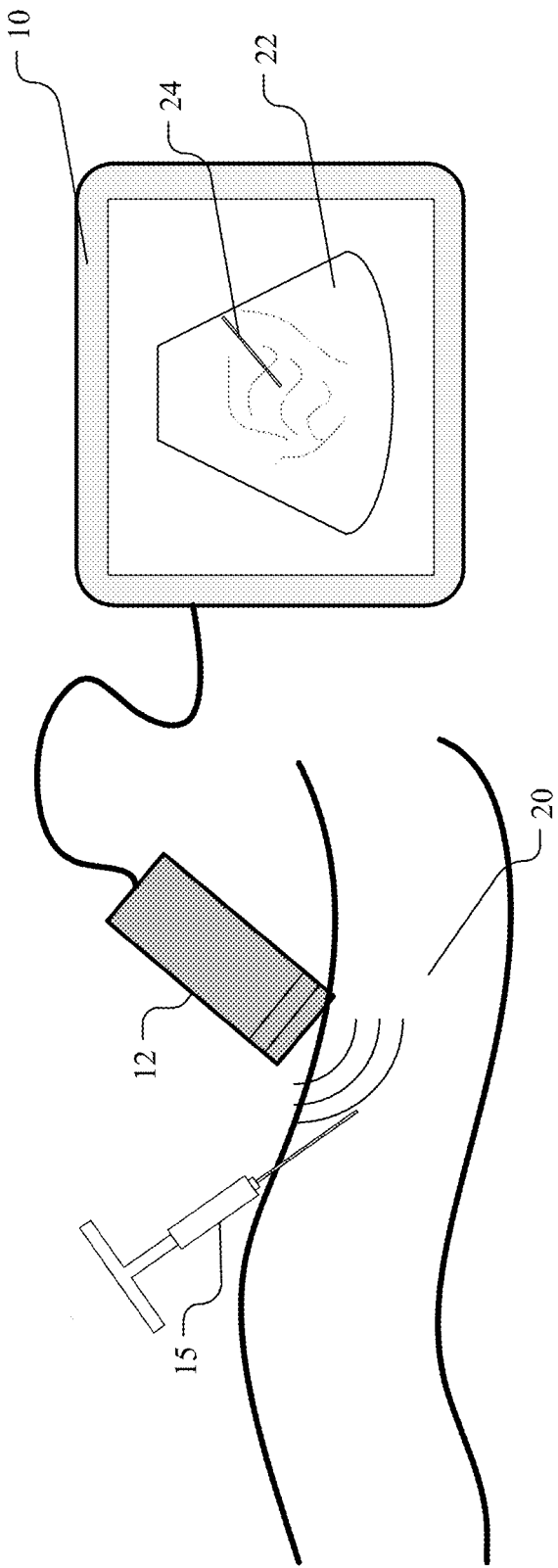
FIG. 1 depicts a simplified illustration of an example ultrasound imaging system for producing and displaying a blended image of tissue and an interventional instrument.

FIG. 1 depicts a representative ultrasound imaging system that implements the disclosed technology for imaging the tissue of a patient. In particular embodiments, an ultrasound imaging system 10 may be a hand-held, portable or cart-based system that uses a transducer probe 12 to transmit ultrasound signals into a region of interest and to receive the corresponding echo signals in order to produce an image of the tissue being scanned. The probe 12 may be a one or two dimensional linear or curved transducer or a phased array transducer all of which can selectively change the steer angles electronically.

The ultrasound imaging system 10 may convert characteristics of the received echo signals (e.g. their amplitude, phase, power, frequency shift etc.) into data that is quantified and displayed for the user as an image. The images created may also be stored electronically for digital record keeping or transmitted via a wired or wireless communication link to another device or location. In particular embodiments, an operator may guide an interventional instrument 15 into the patient (or subject) 20 with one hand while holding the probe 12 with the other hand. The ultrasound imaging system 10 may automatically detect the presence of the interventional instrument 15, and determine one or more needle frames that best depicts the location of the interventional instrument 15. The operator may view a composite image 22 of the tissue and a representation 24 of where the interventional instrument is located in the tissue. The composite image 22 may be updated on the screen while the instrument is guided to the target location. Such a location may be a particular nerve site in the field of anesthesia or other area of interest such as a vessel or a particular organ (e.g. uterus, prostate, tumor, heart vessel etc.).

As may be understood by those skilled in the art, the optimal beam direction for imaging a long thin interventional instrument (such as a needle) may be at an angle that is approximately perpendicular to the length of the instrument. However, the imaging parameters and beam directions required to image an instrument may not often be the same as those that are optimal for imaging the tissue. In particular embodiments, the user may not be required to select a particular beam angle to use in generating the needle frames. Instead, the processor may be programmed to generate needle frames using multiple different steer angles. The echo data for the needle frames created from these different steer angles may be analyzed to detect the presence of objects that may be an interventional instrument. In particular embodiments, detection of interventional instruments and determination of the best needle frame steer angle for visualization of the interventional instrument may be determined via a trained machine-learned algorithm. As an example and not by way of limitation, a trained neural network may analyze one or more ultrasound images to determine whether an interventional instrument is present, and the appropriate angle to capture the interventional instrument so that a needle frame may be combined with the anatomy image to create a composite frame. In particular embodiments, echo data from one or more of the needle frames obtained using different transmit beam directions and that likely represent an interventional instrument may be copied from the needle frames and blended with the echo data for the anatomy image in order to produce the composite image that shows both the tissue and the position of the interventional instrument.

Figure 2:
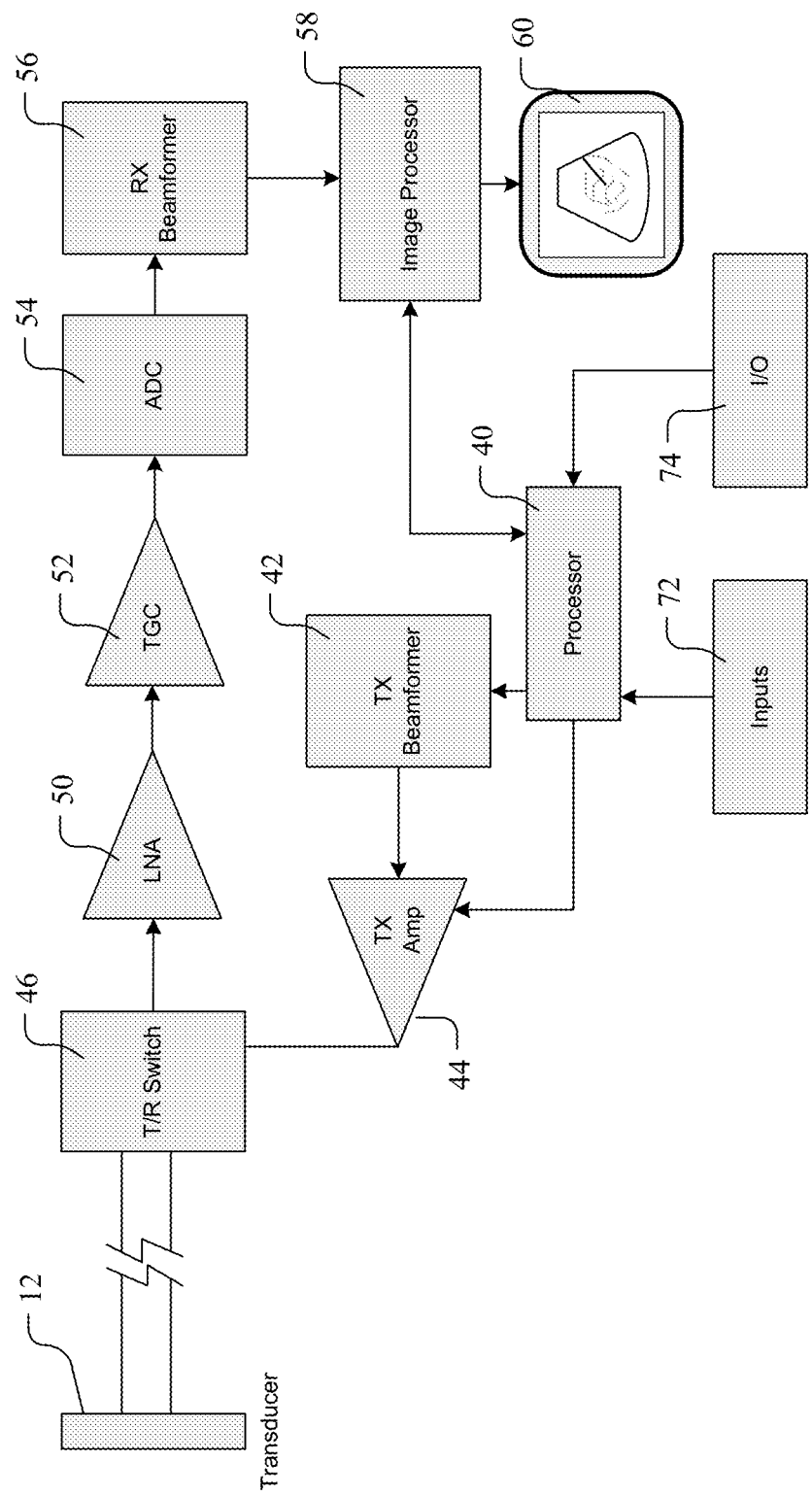
FIG. 2 depicts a block diagram of an example ultrasound imaging system.

FIG. 2 depicts a simplified block diagram of an ultrasound imaging system in accordance with an embodiment of the disclosed technology. In particular embodiments, the ultrasound system may be constructed with components that are different than those shown. In addition, the ultrasound system may include parts that are not discussed (e.g. a power supply etc.) and that are not necessary for the understanding of how to make and use the disclosed technology. In the embodiment shown, the ultrasound system may include a processor 40 having a built-in or external memory (not shown) containing instructions that are executable by the processor to operate the ultrasound imaging system as will be explained in detail below. In the transmit path, the ultrasound system may include a transmit beamformer 42, a transmit gain control amplifier 44 and a transmit/receive switch 46. If the ultrasound probe 12, is a phased array type or can otherwise change the angle of transmissions electronically, the transmit beamformer 42 may operate to generate a number of signals having a relative amplitude and phase (timing) that are selected to produce an ultrasound beam from some or all of the transducer elements of the probe that constructively add in a desired transmit beam direction (the desired steer angle). The signals from the transmit beamformer may be amplified by the transmit amplifier 44 to a sufficiently high voltage level that will cause the transducer elements to produce the desired acoustic signals in the tissue being examined. In particular embodiments, the processor 40 may be connected to supply a control command such as a digital value (e.g. 0-255) to the gain control amplifier. The value of the command may control the amount of gain that is supplied by the transmit amplifier 44.

Other techniques for adjusting the power of the ultrasound signals may include changing the waveforms that drive the transducer elements to either increase or decrease the power of the ultrasound signals. In particular embodiments, the voltage rails (+V, −V) of an amplifier that produces the driving signals may be changed in order to vary the power of the ultrasound signals. In particular embodiments, driving signals may be supplied to a lessor or a greater number of transducer elements to change the power of the ultrasound signals. Those skilled in art may understand that these techniques are merely exemplary and that there may be numerous ways in which the level of acoustic power of the ultrasound signals delivered to the patient can be adjusted.

In particular embodiments, the amplified transmit signals may be supplied to the transducer probe 12 through the transmit/receive switch 46, which disconnects or shields sensitive receive electronics from the transmit signals at the time they are delivered to the transducer probe 12. After the signals are transmitted, the transmit/receive switch 46 may connect the receive electronics to the transducer elements to detect the corresponding electronic echo signals created when the returning acoustic waves impinge upon the transducer elements.

In particular embodiments, in the receive path, the ultrasound imaging system may include a low noise amplifier 50, a time gain control (TGC) amplifier 52, an analog to digital converter 54, a receive beamformer 56 and an image processor 58. Analog echo signals produced by the imaging probe may be directed through the transmit/receive switch 46 to the low noise amplifier where they are amplified. The TGC amplifier 52 may apply a variable amplification to the received signals that varies the level of amplification applied with the return time of the signals (e.g. proportional to the depth in the tissue being imaged) to counteract the attenuation of the signals versus depth. The amplified signals may then be converted into a digital format by the analog to digital converter 54. The digitized echo signals may then be delayed and summed by the receive beamformer 56 before being supplied to the image processor.

In particular embodiments, the number of transmitted beams and received beams (lines) may differ from each other. As an example and not by way of limitation, the receive beamformer may produce in parallel (i.e., simultaneously) two or more adjacent lines per transmitted beam, a technique sometimes known as parallel receive beamforming or multi-line processing. Multi-line processing may be used to increase the imaging frame rate by lowering the number of transmitted beams while still being able to keep the number of received lines per frame (line density) constant. In particular embodiments, a higher multi-line order (number of receive lines beamformed in parallel from a single transmitted beam) may be used to increase the number of received lines per frame while keeping the number of transmitted beams, hence the frame rate, constant. Other combinations of line density, frame rate and multi-line order may also be possible. Furthermore, it may be possible to transmit an unfocused beam (plane wave) and beamform all the receive lines of a frame from that single transmitted beam. The system may also employ different combinations of line density and multi-line order for imaging the tissue vs. imaging an interventional instrument. In particular embodiments, use of a higher multi-line order, a lower-line density, or unfocused transmit beams, while improving the frame rate, may reduce the quality of the acquired images.

Images produced by the image processor 58 from the received signals may be displayed on a display 60. In addition, the images may be recorded in an image memory (not shown) for future recall and review. A number of inputs 72 may be provided to allow an operator to change various operating parameters of the ultrasound imaging system and to enter data such as the patient's name or other record keeping data. In addition, the ultrasound imaging system may include input/output (I/O) circuitry to allow the system to connect to computer communication links (LAN, WAN, Internet etc.) through a wired (e.g. Ethernet, USB, Thunderbolt, Firewire, or the like) or wireless (802.11, cellular, satellite, Bluetooth or the like) communication link.

The details of the components that comprise the ultrasound imaging system and how they operate may be generally considered to be well known to those of ordinary skill in the art. Although the ultrasound imaging system is shown having many separate components, devices such as ASICs, FPGAs, digital signal processors (DSPs), CPUs or GPUs may be used to perform the function of multiple ones of these individual components.

As discussed above, the processor 40 may be programmed to create a composite image of the tissue being examined and an interventional instrument being introduced into the tissue. In particular embodiments, the image processor may produce an anatomy image of the tissue being examined with imaging parameters that are selected for the depth and particular type of tissue being scanned. The anatomy image created by the image processor 58 may be stored in memory to be combined with echo data for one or more of the needle frames that are created to locate an interventional instrument.

In one embodiment, the processor may cause the transmit electronics to produce transmit beams in a number of different transmit directions to image the interventional instrument. As an example and not by way of limitation, the processor 40 may direct transmit beams to be produced at a shallow, medium and steep angle as measured with respect to a longitudinal axis of the transducer probe. In particular embodiments, the position of the interventional instrument may show more clearly in one or more of the needle frames than in the others. An example needle visualization technique is depicted in commonly-owned U.S. patent application Ser. No. 15/347,697, filed 9 Nov. 2016, which is incorporated herein by reference.

In particular embodiments, the echo data for each of the needle frames created from the transmissions at the different transmit angles may be analyzed for the presence of an interventional instrument. Various instrument detection algorithms may be used. As an example and not by way of limitation, the images may b e analyzed for the presence of a linear segment of pixels that are much brighter (e.g. greater amplitude) than adjacent pixels thereby indicating the presence of a strong linear reflector. The length of the segments that may represent an interventional instrument may vary and in some embodiments, may be curved if the interventional instrument itself is curved or bends when the instrument is inserted. Alternatively, the segments may seem to be curved in the coordinate system where detection is performed if the images were acquired using a curved transducer geometry (e.g., convex).

In particular embodiments, each segment of bright pixels may be scored to indicate how likely the segment represents an interventional instrument. As an example and not by way of limitation, such a score may be adjusted by the length of the bright pixels above a certain threshold, how straight or linear the segment of pixels is, how much contrast is present between the bright pixels and the adjacent pixels, how strong the edges around the segment of bright pixels are as determined by a gradient or other edge-detection operations, etc. A Hough transform or other similar techniques may be used to determine the location of pixels that lie on a linear or parameterized curved segment, from which a score may also be determined.

In particular embodiments, the brightness data values for an image may be converted into corresponding gradient values by looking at differences between adjacent brightness values along the beam lines. A needle or other bright reflector that is an interventional instrument may be generally characterized by a large positive gradient (e.g. dark to light) in brightness values followed closely by a large negative gradient (e.g. light to dark) of brightness values when viewed in the direction from the transducer and into the tissue. The gradient values may be filtered to ensure that the large changes in the positive and negative gradient values occur within a distance that would be expected for the interventional instrument. Next, a Hough transform may be used to determine if the large positive/negative gradient changes occur in a linear pattern in the adjacent beam lines. Scores for the segments of large gradient changes may be increased or decreased depending on one or more of the length of the gradient changes, how close a positive gradient change is from a negative gradient change, how the gradient changes align spatially from beam to beam.

In particular embodiments, segments of echo data may be scored according to how large the gradients are and how well the gradients align in adjacent beam lines. Those segments having larger gradients and being more in line may be given greater scores than those with smaller gradients and being less aligned. A representation of an instrument may comprise a single long segment or multiple shorter segments, and not all segments having the highest score may originate from the same needle frame.

In particular embodiments, echo data representing likely interventional instruments from those images with the highest scoring segments may be copied from two or more needle frames and blended with the echo data for the anatomy image. In another embodiment, echo data may be copied from a single needle frame and blended with the echo data for the anatomy image. In particular embodiments, other needle visualization techniques for detecting the presence of a needle or other interventional instrument in an ultrasound image may also be used.

In particular embodiments, the processor may be programmed to identify segments of pixel data from one or more of the needle frames created from the transmissions taken at the various transmit angles that have a score that indicates the pixels likely represent an interventional instrument. The processor may copy the pixel data representing the instrument and uses a blending function to combine the copied pixel data with the pixel data in the anatomy image.

In particular embodiments, the pixel data used to display the ultrasound images may be analyzed to detect the presence of an interventional instrument. In particular embodiments, the echo data may be analyzed prior to conversion into pixel data that is ready for display. As an example and not by way of limitation, echo data that has been amplified, converted to digital and beamformed but not yet scan converted may be analyzed to detect and score segments in the data that represent interventional instruments.

In particular embodiments, creating a number of needle frames at different transmit angles may decrease the frame rate of the ultrasound imaging system. In particular embodiments, the processor may select a higher line density and/or a lower multi-line setting for a subset of the needle frames (e.g. high-quality needle frames) than the rest of the needle frames (lower-quality needle frames), where the high-quality needle frame(s) is/are chosen adaptively based on the orientations of structures detected by the instrument detection algorithm with a high score (i.e. a high probability for the presence of an interventional instrument). If the detection algorithm finds structures of a similar orientation with high scores in multiple needle frames, the needle frame with an imaging steering angle that would insonate an interventional instrument at a close-to-perpendicular angle to the orientation of the probe may be chosen to be a high-quality needle frame acquisition and the other needle frames may continue to be acquired as lower quality needle frames. The adaptive selection of the high-quality needle frame may ensure a high quality visualization of the "most-probable" interventional instrument while the remaining lower-quality needle frames may ensure that instruments at other orientations are not missed, and that an operator may not be required to manually select a high-quality needle frame if the angle of the interventional instrument with respect to the ultrasound scan head changes during the procedure.

In particular embodiments, the system may also alter the number and acquisition rate of the needle frames and the angles employed adaptively based on the detection scores. As an example and not by way of limitation, if features with high detection scores are identified within a needle frame with a certain angle setting, the system may designate that angle as a "high priority angle" and increase the acquisition rate of needle frames at or close to that angle setting, while dropping the acquisition rate of needle frames at angles farther away from the high-priority angle or for needle frames that do not contain features with high segment scores. In particular embodiments, the system may continue to acquire and analyze needle frames that have angles farther away from the high-priority angle setting as "scouting" needle frames so that the system may re-assess and change the "high-priority angle" on the fly if features with higher detection scores are detected with those scouting needle frames at any time. In particular embodiments, the angles of the scouting needle frames may be selected to have a larger angle spread between them and/or a lower acquisition rate to minimize the overall impact to the frame rate.

Figure 3:
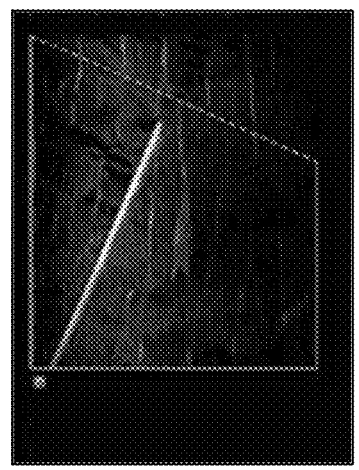
FIG. 3 depicts an example of multiple ultrasound images taken at multiple angles to determine the most suitable angle for a needle frame.
Figure 3:
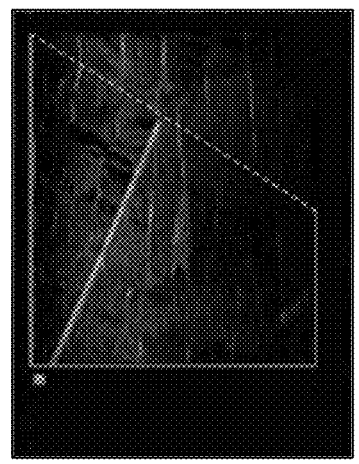
Figure 3:
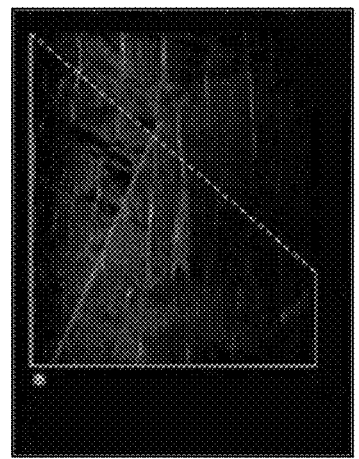

FIG. 3 depicts an example of three needle frame images taken by the ultrasound imaging system. In the example of FIG. 3, the needle frame images may be taken at shallow, medium, and steep angles. In particular embodiments, each of the needle frame images may be at a steeper angle than the images normally taken for B-mode frames. In each of the three needle frames depicted in FIG. 3, the interventional instrument (for example, a needle) may be visible in the frame. In FIG. 3, the needle frame captured at the shallow angle may show the needle more clearly compared to the medium and steep angles. In this example, it may be seen that the needle is perpendicular to the angle of the shallow frame's transmit beams, while the needle is not quite perpendicular to the angles of the transmit beams of the medium and steep frames. In particular embodiments, the angles used for the needle frame images may be too steep to create an image of the anatomical structures within the ultrasound image's field of view.

Figure 4:
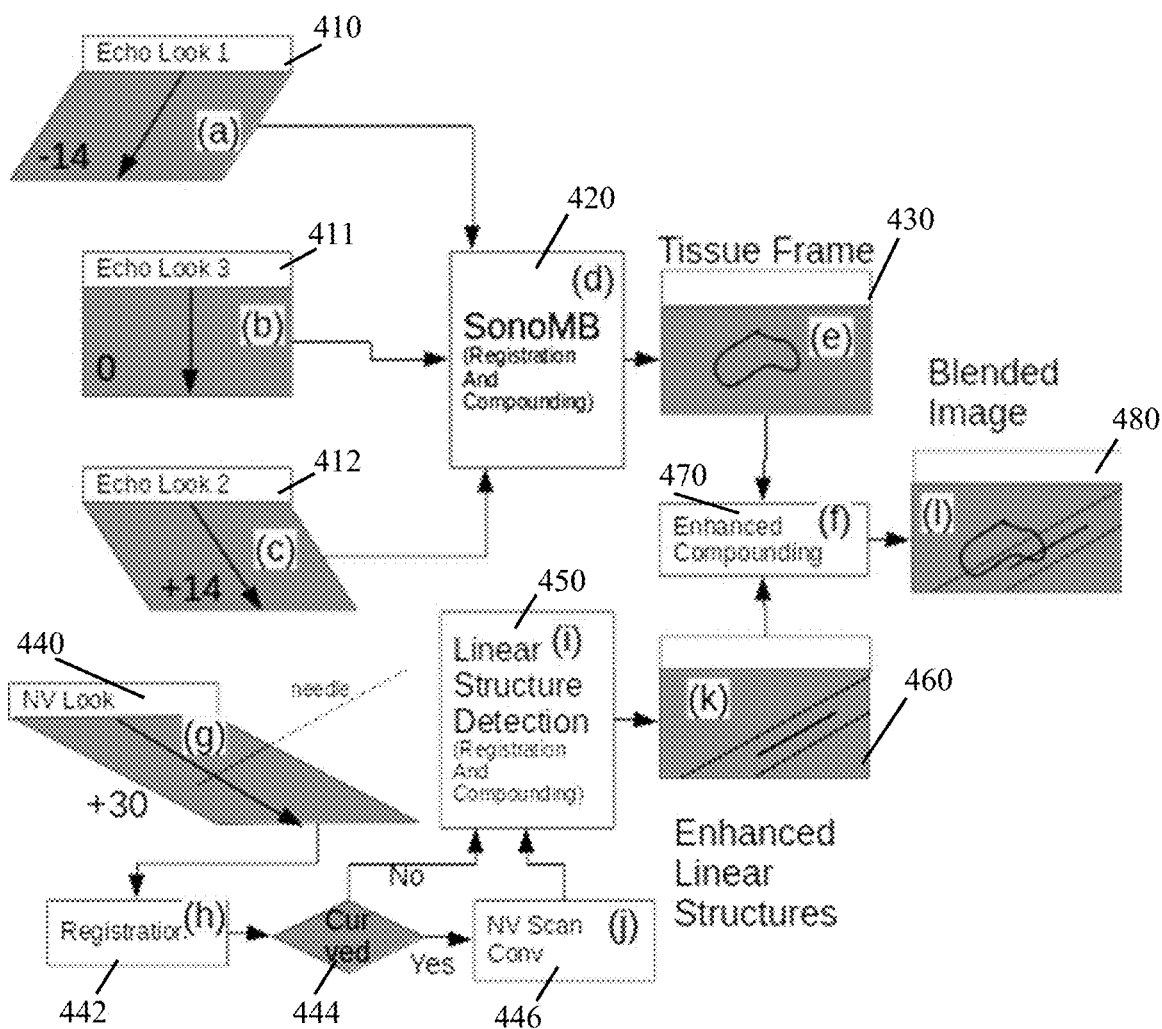
FIG. 4 depicts an example diagram of an ultrasound imaging system that may produce and display a blended image of tissue and an interventional instrument.

FIG. 4 depicts an example system for creating a blended image combining a composite tissue frame and a linear structure corresponding to an interventional instrument (for example, a needle). In the example of FIG. 4, the ultrasound imaging system may capture three frames 410, 411, and 412 to be used to determine the tissue frame. In particular embodiments, the three frames 410, 411, and 412 are taken at different transmit beam directions, but directed at the same anatomical structure. As an example and not by way of limitation, frame 410 may be taken at an angle of −14 degrees, frame 411 may be taken at an angle of 0 degrees, and frame 412 may be taken at an angle of +14 degrees. In particular embodiments, the angles used for frames 410, 411, and 412 may be shallower than the angles needed to visualize an interventional instrument. In particular embodiments, the angles used for frames 410, 411, and 412 may be those appropriate for brightness mode, or B-mode, ultrasound images. As an example and not by way of limitation, 3 or 5 image frames may be captured in order to create a B-mode image to reduce speckle, wherein at least one frame is captured at 0 degrees, and the other frames are taken between −15 and +15 degrees. At step 420, the ultrasound imaging system make combine the frames 410, 411, and 412, to create a composite tissue frame 430 depicting the anatomical structures within the field of view. In particular embodiments, frames 410, 411, and 412 may be image frames appropriate for one or more other modes of imaging, such as color mode. In particular embodiments, frames 410, 411, and 412 may change settings over time such that frames appropriate for a first image mode may be interleaved with frames appropriate for a second image mode.

In particular embodiments, the ultrasound imaging system may also capture a needle frame 440, which may be captured at a steeper angle to enhance visualization of interventional instruments. In particular embodiments, the user of the ultrasound imaging system may manually select an option to capture one or more needle frames. In such an embodiment, the user may input whether to angle the image to the left or to the right, and the user may input the steer angle of the needle frame. In the example of FIG. 4, ultrasound image frame 440 is taken at an angle of +30 degrees, which may be better suited to reflect the ultrasound signals off the shaft of the interventional instrument. At step 442, the ultrasound imaging system determines that a structure is present, and at step 444, determines whether the imaging probe is linear or curved, if the probe is curved, then at step 446, the ultrasound imaging system performs scan conversion. At step 450, the ultrasound imaging system may determine that a linear structure corresponding to an interventional instrument exists, and its location within the ultrasound images. The ultrasound imaging system may then generate a linear structure image 460 that depicts the interventional instrument with a masked region defined around the linear structure within the same field of view as composite tissue frame 430. At step 470, the ultrasound imaging system may merge the composite tissue frame 430 with the linear structure 460 within the masked region to generate a blended image 480, which depicts the enhanced interventional instrument and its relative position to the imaged anatomical structures.

Figure 5:
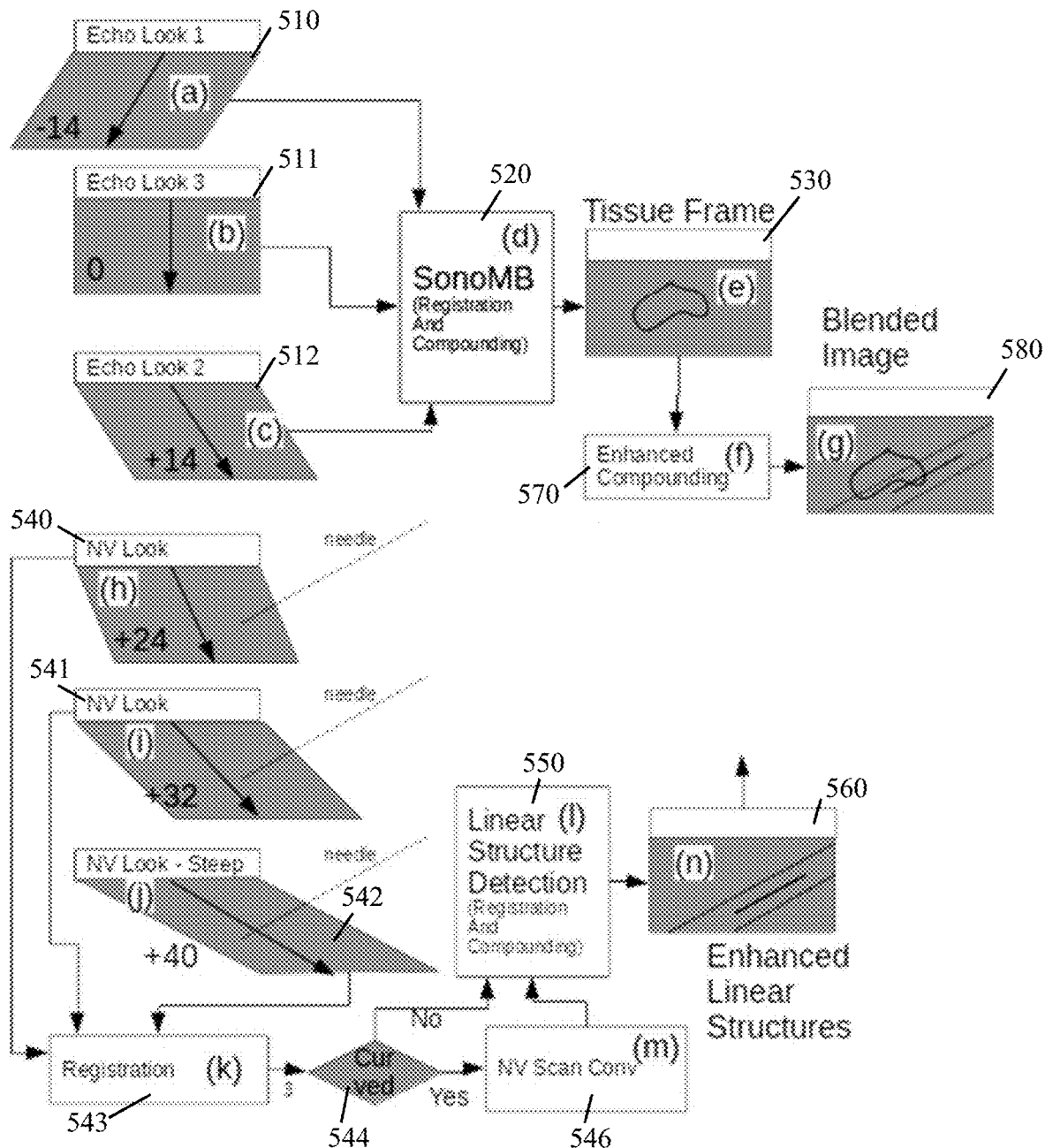
FIG. 5 depicts an example diagram of an ultrasound imaging system that may automatically select an optimal needle frame from a plurality of steer angles, and produce and display a blended image of tissue and an interventional instrument.

FIG. 5 depicts another example system for creating a blended image combining a composite tissue frame and a linear structure corresponding to an interventional instrument. In the example of FIG. 5, the ultrasound imaging system may capture a plurality of needle frames, and determine which is most suitable for combining into the blended image. In FIG. 5, similarly to FIG. 4, the ultrasound imaging system may capture three frames 510, 511, and 512, at multiple angles suitable for combining into a B-mode image. At step 520, the ultrasound imaging system may combine the frames 510, 511, and 512 into a composite tissue frame 530 for spatial compounding. Upon receiving an indication from the user that an interventional instrument is present, and the direction from which the interventional instrument is being introduced, the ultrasound imaging system may capture multiple needle frames 540, 541, and 542, from different angles. In the example of FIG. 5, needle frame 540 is captured at a steer angle of +24 degrees; needle frame 541 is captured at a steer angle of +32 degrees; and needle frame 542 is captured at a steer angle of +40 degrees. In particular embodiments, the angles for the shallow, medium, and steep needle frames may be predetermined by the ultrasound imaging system, or preset by the user.

In the example of FIG. 5, the ultrasound imaging system then determine which of needle frames 540, 541, and 542 are appropriate for determining the linear structure. In particular embodiments, the ultrasound imaging system determines which of the needle frames most prominently shows the presence of an interventional instrument by choosing the frame with the highest linear structure score. At step 543, the ultrasound imaging system determines that a structure is present in one or more of the needle frames, and at step 544, determines whether the imaging probe is linear or curved. If the probe is curved, then at step 546, the ultrasound imaging system performs scan conversion. At step 550, the ultrasound imaging system may determine that a linear structure corresponding to an interventional instrument exists, and its location within the ultrasound images. In particular embodiments, the ultrasound imaging system may determine which of needle frames 540, 541, and 542 should be used for the enhanced linear structure, and may remove the unselected needle frames from consideration. The ultrasound imaging system may then generate an enhanced linear structure image 560 that depicts the interventional instrument (at the selected needle frame angle) with a masked region defined around the linear structure within the same field of view as composite tissue frame 530. At step 570, the ultrasound imaging system may merge the composite tissue frame 530 with the enhanced linear structure 560 to generate a blended image 580, which depicts the interventional instrument and its relative position to the imaged anatomical structures.

In particular embodiments, an advantage to the system of FIG. 5 over systems such as those depicted in FIG. 4 may be that the user doesn't have to determine the steer angle for depicting the line structure and because multiple needle frames are used, the ultrasound imaging system may dynamically determine the best angle for depicting the interventional instrument over time, and switch the needle frame angle used as needed. In particular embodiments, a potential downside to the system of FIG. 5 may be that because three needle frames must be captured for each set of composite tissue frames (which themselves are a combination of three frames), the system of FIG. 5 may require at least six total frames be captured in order to generate a single blended image, which may reduce the frame rate of the ultrasound imaging system.

Figure 6A:
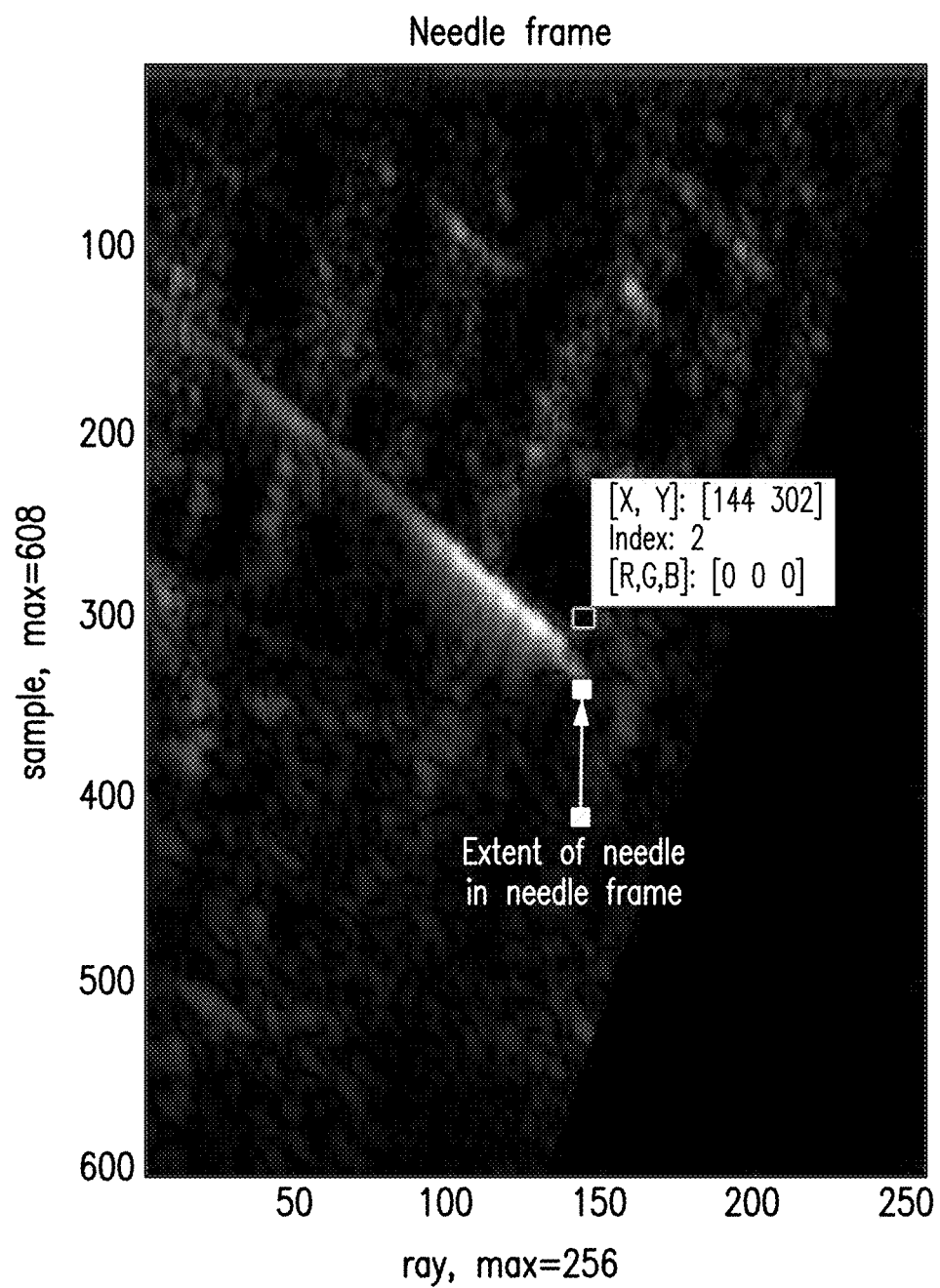
FIGS. 6A-6C depicts an example of a needle frame image being combined with a tissue frame to produce a blended image for display.
Figure 6B:
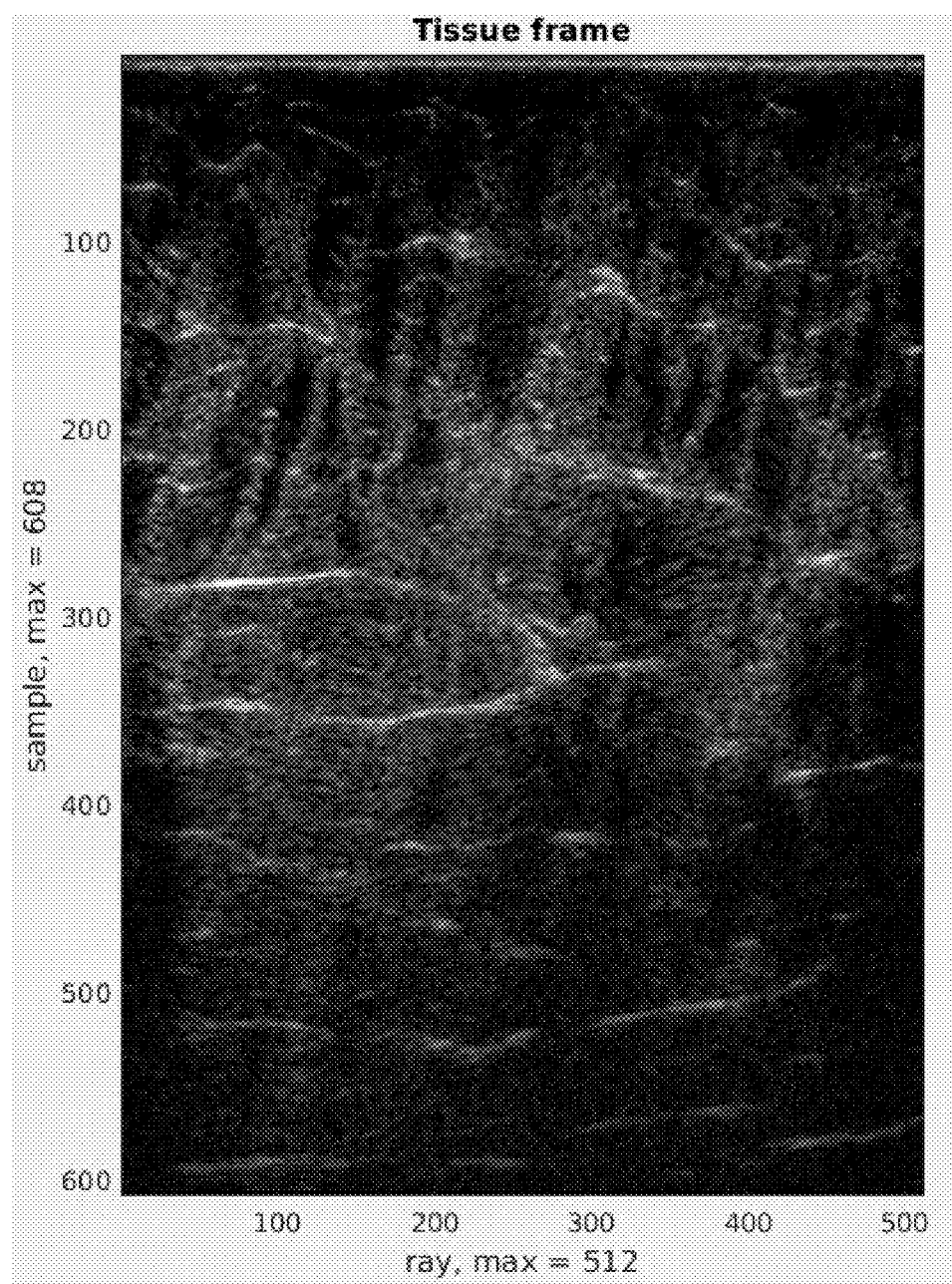
Figure 6C:
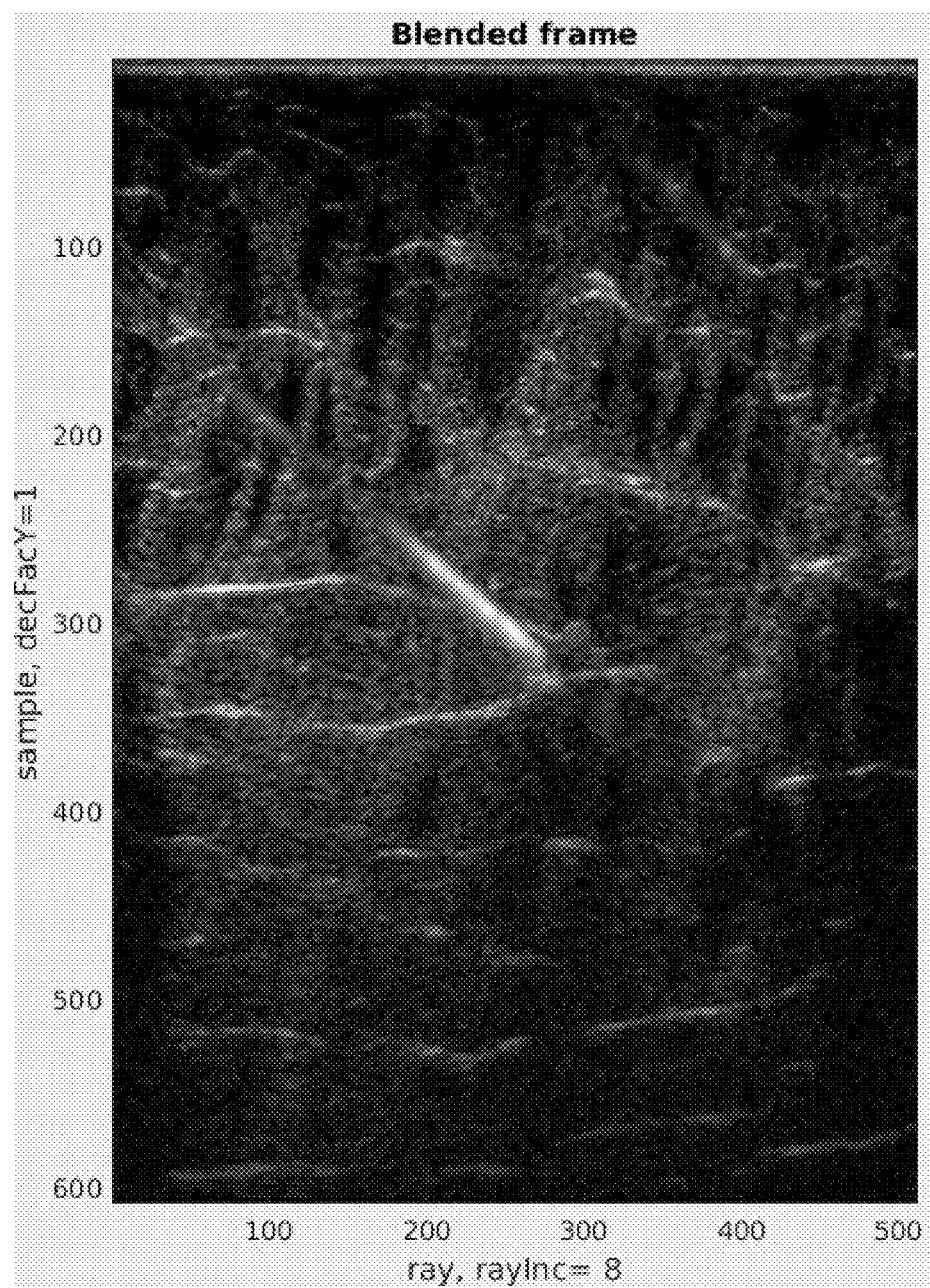

FIGS. 6A-6C depict example images of needle frames and composite tissue frames that may be combined by the ultrasound imaging system into a blended image. FIG. 6A depicts a needle frame, where a linear structure corresponding to an interventional instrument is visible in the middle of the frame. In particular embodiments, the ultrasound imaging system may determine the extent of the interventional instrument within the needle frame. As an example and not by way of limitation, the x-coordinate corresponding to the left-most or right-most portion of the linear structure may be determined. FIG. 6B depicts a composite tissue frame depicting the anatomical structures present in the same field of view as the one depicted in FIG. 6A. FIG. 6C depicts the blended image combining the needle frame of FIG. 6A and the composite tissue frame of FIG. 6B. A user viewing the blended image of FIG. 6C may be able to visualize the interventional instrument in relation to the anatomical structures within the composite tissue frame.

In particular embodiments, the ultrasound imaging system may be able to automatically detect whether an interventional instrument has been inserted into the anatomical structure from the left side, or from the right side. As an example and not by way of limitation, a user may indicate through user input on the ultrasound imaging system that an interventional instrument is being used with the anatomical feature of interest. The user may then insert the interventional instrument without specifying the direction from which the interventional instrument is being asserted. The ultrasound imaging system may receive one or more B-mode frames for creation of the composite tissue frame, as well as one or more needle frames depicting the position of the interventional instrument.

In particular embodiments, the ultrasound imaging system may detect the presence of an interventional instrument from the B-mode frames alone. As an example and not by way of limitation, the ultrasound imaging system may detect tissue warping in the B-mode frames that is consistent with a right-side entry of a needle into the frame. In particular embodiments, "left" and "right" side entry may be determined from the perspective of the user. In particular embodiments, "left" and "right" side entry may be determined from the perspective of the ultrasound probe. In particular embodiments, it may be appreciated that the specific terms for entry from one direction relative to the tissue or the other is irrelevant so long as the user is consistently aware of which term refers to which direction. For the examples discussed in this application, "left" and "right" are used and may be understood to refer to the two opposite directions from which needle entry is possible. As another example, the ultrasound imaging system may compare B-mode frames over time, and detect movement corresponding to a left-side entry of an interventional instrument. In particular embodiments, based on the detection of left or right entry of the interventional instrument, the ultrasound imaging system may automatically capture one or more needle frames from angles corresponding to the detected side. As an example and not by way of limitation, if the ultrasound imaging system determines from the B-mode frames that there is a left-side entry of a needle, the ultrasound imaging system may capture three needle frame images corresponding to a left-side entry at shallow, medium, and steep angle images suitable for left side entry and then determines the linear structure corresponding to the needle using all three images.

In particular embodiments, the ultrasound imaging system may use a set of exploratory needle frames to detect left or right-side entry of the interventional instrument. As an example and not by way of limitation, prior to detection of the interventional instrument, the ultrasound imaging system may take a plurality of B-mode frames (e.g. three B-mode frames) in order to generate the composite tissue frame for display, followed by a left-side medium-angle needle frame, then followed by a right-side medium angle needle frame. As another example, the ultrasound imaging system could further capture a third needle frame, wherein the third needle frame cycles from a left-side needle frame and a right-side needle frame. In particular embodiments, the overall frame rate for capturing three B-mode frames followed by three needle frames may be similar to the frame rate when the ultrasound imaging system is automatically determining the best angle for the needle frame, which also utilizes three B-mode frames and three needle frames.

In particular embodiments, the ultrasound imaging system may capture a first set of ultrasound image frames of the target tissue region, where the first set corresponds to a plurality of B-mode, color mode, or other suitable image frames for depicting the tissue in the target region. As an example and not by way of limitation, the steer angles for the first set of ultrasound image frames may be −14, 0, and +14 degrees, where in this example, 0 degrees depicts the angle at which the transmit beam of the ultrasound imaging system is perpendicular to the ultrasound transducer of the ultrasound imaging system. An example coordinate system of positive, negative, and zero steer angle is depicted in FIGS. 4 and 5. In particular embodiments, the specific assignment of "positive" steer angle to a particular direction and "negative" steer angle to the other direction may not be important so long as the system and user is able to distinguish that they are opposite each other. The ultrasound imaging system may then capture a second set of ultrasound image frames following the first set. The second set of ultrasound image frames may use steer angles that are steeper than the first set, which may be more appropriate for imaging an interventional instrument such as a needle. As an example, the second set of ultrasound image frames may be taken at steer angles of −32, +24, and +32 degrees. In particular embodiments, the second set of ultrasound image frames may include at least one frame taken from a first side of the zero angle (i.e. negative steer angles), and at least one frame taken from the opposite, second side (i.e. positive steer angles). In particular embodiments, the second set of ultrasound image frames may alternate the ratio of steer angles for a subsequent series of frames. As an example and not by way of limitation, if a prior second set of ultrasound image frames used −32, +24, and +32 degrees, a subsequent second set may use −32, −24, and +32 degrees. In particular embodiments, an even number of second set frames may be captured, and each second set may capture an equal number of negative- and positive-angle ultrasound image frames.

In particular embodiments, based on the second set of ultrasound image frames, the ultrasound imaging system may determine whether an interventional instrument such as a needle is present in one or more of the images. In particular embodiments, if none of the second set of ultrasound image frames depicts an interventional instrument, the imaging sequence continues as described above. In particular embodiments, if an interventional instrument is detected, the ultrasound imaging system may then determine whether the interventional instrument is depicted with a left-side entry (e.g. depicted in the negative-angle images) or right-side entry (e.g. depicted in the positive-angle images). Because the image of an interventional instrument may be stronger when the steer angle is perpendicular or nearly perpendicular to the primary axis of the interventional instrument (such as the shaft of a needle), the interventional instrument will be depicted much more strongly in one direction than the other (where the steerangle would instead be closer to parallel with the interventional instrument). In particular embodiments, once a direction is selected, the ultrasound imaging system may create composite tissue frames to visualize the interventional instrument by using the first set of ultrasound image frames for the tissue, and one or more ultrasound image frames taken to depict the interventional instrument. In particular embodiments, the one or more ultrasound image frames may be images already captured in the second set. In particular embodiments, the ultrasound imaging system may determine that additional images are necessary to capture the interventional instrument. The ultrasound imaging system may determine a new steer angle for the additional images that may better depict the interventional instrument compared to the second set images.

In particular embodiments, upon detection of an interventional instrument and the direction of entry of the interventional instrument, the ultrasound imaging system may adjust the direction and steer angles of the second set of ultrasound image frames for subsequent images. For example, if a prior set of images indicates that an interventional instrument is detected with right-side entry best captured at +32 degrees, then the ultrasound imaging system may capture subsequent second sets only in the positive direction or always include a steer angle of +32 degrees, to blend with the composite tissue frame depicting the interventional instrument. In this example, the ultrasound imaging system may eliminate the number of negative steer angle frames captured (i.e. consistent with left-side entry), since the interventional instrument has already been detected with right-side entry. In particular embodiments, the ultrasound imaging system may cease capturing left-side frames for the second set once right-side entry is determined, and only capture right-side entry frames moving forward. In particular embodiments, the ultrasound imaging system may continue the normal process for capturing the second set of ultrasound image frames until multiple second sets confirm that an interventional instrument is present, and the direction of entry. As an example and not by way of limitation, if one second set of ultrasound image frames indicates left-side entry, the ultrasound imaging system may still not determine that there is left-side entry of an interventional instrument until two subsequent sets of ultrasound image frames also indicates left-side entry.

In particular embodiments, it may be further advantageous for the ultrasound imaging system to automatically detect whether an interventional instrument is present in the field of view of the anatomy image, without input from the user indicating that an interventional instrument is being introduced into the field of view. In particular embodiments, the automatic detection of an interventional instrument may be combined with an automatic determination of left or right-side entry of the interventional instrument, and automatic identification of shallow, medium, or steep angle as the optimal needle frame. An advantage of such an embodiment may be that the user does not need to provide any additional inputs to start imaging the interventional instrument—once the user inserts the interventional instrument, the ultrasound imaging system may detect the instrument, determine direction and angle, detect the linear structure by capturing needle frames at the appropriate direction and angle, and generate the blended image for display.

In particular embodiments, automatic detection may be performed by having the ultrasound imaging system always capture at least one needle frame image in addition to B-mode frames. In particular embodiments, once the ultrasound imaging system determines that an interventional instrument is present, the ultrasound imaging system may initiate capture of additional needle frames to determine the direction of entry, and identify the optimal angle for imaging the interventional instrument. In particular embodiments, automatic detection of the interventional instrument may be initiated by analysis of the B-mode frames alone, without needle frames. As an example and not by way of limitation, a needle may be detected on an angled B-mode frame (e.g. +15 degrees) at a quality that is not sufficient for accurate visualization and display, but sufficient to determine that an interventional instrument has been inserted, and from which direction.

In particular embodiments, the ultrasound imaging system may utilize one or more classifier algorithms to determine whether an interventional instrument is present in the anatomy image, without utilizing a needle frame image. In particular embodiments, a classifier algorithm may rely on artificial intelligence, machine-learning, neural networks, or any other suitable algorithm to analyze the ultrasound images. As an example and not by way of limitation, a classifier algorithm may detect tissue warping in the anatomy image that occurs over time due to the movement of the interventional instrument affecting the surrounding tissue. As another example and not by way of limitation, the classifier algorithm may be trained to classify images depicting non-cyclic temporal changes in the anatomy image as potentially containing an interventional instrument. In such an example, the classifier algorithm would determine whether changes in the anatomy image over time are due to periodic movements (such as a heartbeat), and disregard those movements. In particular embodiments, the classifier algorithm may receive positive feedback for detecting temporal changes in the anatomic structure corresponding to insertion of an interventional instrument, and negative feedback for detecting temporal changes due to other factors, such as blood flow, heartbeat, or muscle movements.

In particular embodiments, the trained classifier algorithms may be based on a neural network. As may be well understood in the art, a neural network includes a plurality of individual "neuron" algorithms, wherein each neuron is trained to detect specific inputs and output a value when the inputs are detected. A neural network may have a large number of neurons working in parallel, as well as many layers of neurons that iteratively receive inputs from the previous layer and provide an output to the following layer. As an example and not by way of limitation, a neural network may be trained to detect left or right entry of an interventional instrument by inputting a large number of images, as well as information indicating for each image whether an interventional instrument is present, which direction, and which needle frame angle is appropriate. By training the neurons so that the outputs based on the input images correspond to the information known about each image, the neural network may be trained to receive images in the future and perform the classifier algorithms discussed herein. In particular embodiments, using a neural network to develop the classifier algorithms may allow training process to be fully automated, given a sufficient number of labeled training images. In particular embodiments, given enough training images and feedback for training, a neural network may detect any other inputs in the ultrasound images that may be relevant for detecting an interventional instrument and its direction of entry, without requiring an explicit input from a user to look for such an input. In particular embodiments, using a trained classifier algorithm may provide a technical improvement to the ultrasound imaging system in automatically detecting the presence of an interventional instrument, its direction, and selecting a needle frame angle for imaging the interventional instrument.

In particular embodiments, a classifier algorithm may be trained only to detect whether an interventional instrument is present. In particular embodiments, a classifier algorithm may also be trained to identify left or right entry of the interventional instrument. As an example and not by way of limitation, a classifier algorithm may analyze an ultrasound image and return a score ranging from 0 to 1, where 0 indicates "left" and 1 indicates "right." In this example, scores in between 0 and 1 may represent a likelihood that the interventional instrument is to the left or right. In particular embodiments, a classifier algorithm may have a first step of determining whether an interventional instrument is present, then in a second step, if an interventional instrument is present, then determining a score corresponding to whether there is a left-side or right-side entry of the interventional instrument, as described above. In such an embodiment, if at the first step, no interventional instrument is detected, it may be unnecessary to proceed to the second step. In particular embodiments, a threshold score may be required to determine that there is a left-side or right-side entry. As an example and not by way of limitation, if 0 corresponds to "left" and 1 corresponds to "right," then a left-side entry may be determined if the score from the classifier algorithm is less than 0.25, and a right-side entry may be determined if the score from the classifier algorithm is greater than 0.75. The thresholds may be automatically adjusted by the ultrasound imaging system, or may be set by the user. In particular embodiments, a left-side or right-side entry determination may require a threshold score to be met for a plurality of frames. As an example and not by way of limitation, a left-side entry may not be determined until three consecutive frames captured by the ultrasound imaging system return a score from the classifier algorithm within the threshold range for left-side entry. As another example, a right-side entry may be determined if X number of frames within the Y most immediate frames have a score within the threshold range for right-side entry. In such an instance, if 8 out of the last 10 frames captured by the ultrasound imaging system indicate a score corresponding to right-side entry, then the classifier algorithm may determine that there has been a right-side entry of an interventional instrument. In particular embodiments, the classifier algorithm may determine entry on a frame by frame basis. In particular embodiments, if a score is determined by the classifier algorithm, but no threshold score is met for either left-side or right-side entry, the classifier algorithm may determine that no interventional instrument is actually present. In particular embodiments, if no threshold score has been met, the classifier algorithm may determine that additional images must be captured and analyzed in order to confirm that there is an interventional instrument present, and to determine the direction of entry. In particular embodiments, the classifier algorithm may be further trained to identify which of the shallow, medium, and steep needle frames may be most appropriate for creation of the composite image.

In particular embodiments, a set of training images may be used to train the classifier algorithms. As an example and not by way of limitation, simulated ultrasound images may be created through MATLAB or other suitable programs, such that the data in the simulated ultrasound images corresponds to images showing an interventional instrument within tissue. The set of training images may depict interventional instruments at various angles relative to the transducer. In particular embodiments, the set of training images may include simulated needle images overlaid over actual tissue images. In particular embodiments, the set of training images may include in situ images of interventional instruments placed in organic tissue. In particular embodiments, the set of training images may be specific to the type of classifier algorithm being trained. As an example and not by way of limitation, if a classifier algorithm is being trained to detect interventional instruments within angled B-mode images (e.g. at −15 and +15 degrees), the set of training images may comprise labeled B-mode images that may or may not have an interventional instrument. As another example and not by way of limitation, for a classifier algorithm being trained detect tissue warping in the difference frames between a first composite tissue frame and the immediately successive composite tissue frame, the set of training images may comprise labeled difference frames.

Figure 7:
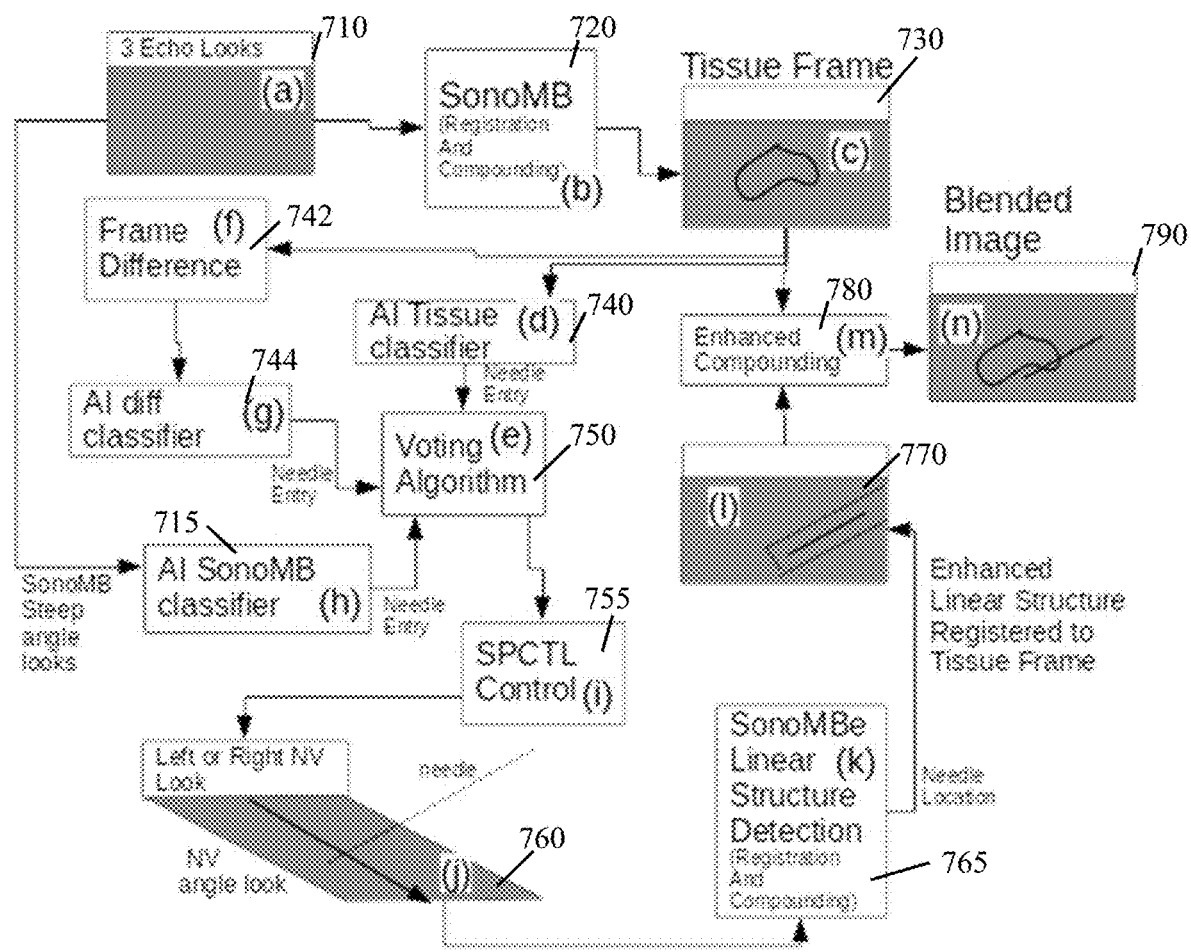
FIG. 7 depicts an example diagram of an ultrasound imaging system that may automatically detect the presence of an interventional instrument as well as the direction of entry, automatically select an optimal needle frame from a plurality of steer angles, and produce and display a blended image of tissue and an interventional instrument.

FIG. 7 depicts an example system for automatically detecting that an interventional instrument is present, detecting whether it is entering from the left or right, determining the appropriate needle frame angle, and creating a blended image with the tissue image and the instrument. The ultrasound imaging system captures a plurality of B-mode frames 710. As an example and not by way of limitation, three B-mode images at −14 degrees, 0 degrees, and +14 degrees may be captured. As another example, five B-mode images may be captured: two angled from the left, two angled from the right, and one at 0 degrees. At step 720, the ultrasound imaging system may combine the plurality of B-mode frames 710 into a composite tissue frame 730. In particular embodiments, composite tissue frame 730 may depict an anatomical structure of interest. In particular embodiments, an interventional instrument may be present while the plurality of B-mode images 710 are captured.

In the example of FIG. 7, a first classifier algorithm 740 may receive as an input the composite tissue frame 730, and determine whether an interventional instrument is present. As an example and not by way of limitation, the first classifier algorithm 740 may detect warping in the composite tissue frame and determine that the warping corresponds to the presence of an interventional instrument. As another example and not by way of limitation, the first classifier algorithm 740 may detect a linear structure in the composite tissue frame in order to determine that an interventional instrument is present. Upon determination that an interventional instrument is present, the first classifier algorithm 740 may output a value indicating whether the interventional instrument is on the left or the right. In particular embodiments, this output is sent to a voting algorithm 750.

The composite tissue frame 730 may further be compared with a previous tissue frame captured and displayed by the ultrasound imaging system. As an example and not by way of limitation, the previous tissue frame may be a composite tissue frame that is most proximate in time prior to the current composite tissue frame 730. Based on this comparison, the ultrasound imaging system may generate a frame difference 742 which represents the temporal change in the composite tissue frame. Frame difference 742 may be input into a second classifier algorithm 744, which is trained to detect an interventional instrument based on temporal changes in the tissue. As an example and not by way of limitation, warping of tissue between the composite tissue frame 730 and the a previous tissue frame may indicate the presence of an interventional instrument, and its location. In particular embodiments, the comparison of two tissue frames may involve two frames that were captured as consecutive frames in time. In particular embodiments, the comparison may use two tissue frames that are separated by a set amount of time, or a set amount of frames. In particular embodiments, the selection of the two tissue frames for comparison may be automatically set by the ultrasound imaging system based on the current image capture settings of the ultrasound imaging system. In particular embodiments, a user may input the parameters for the separation between the two tissue frames being compared.

In particular embodiments, the second classifier algorithm 744 may detect differences using B-mode frames 710 rather than composite tissue frame 730. As an example and not by way of limitation, the second classifier algorithm 744 may detect changes between a recent B-mode frame taken at +14 degrees, and a prior B-mode frame taken at +14 degrees, to determine if a change corresponding to an interventional instrument may be detected. The second classifier algorithm 744 may output a score indicating whether the interventional instrument is to the left or the right, and send the output to voting algorithm 750. In particular embodiments, if the second classifier algorithm 744 does not detect an interventional instrument, it may send no output score to voting algorithm 750. In particular embodiments, if no interventional instrument is detected, the second classifier algorithm 744 may affirmatively indicate to the voting algorithm 750 that it did not detect an interventional instrument.

The plurality of B-mode frames 710 may be sent to a third classifier algorithm 715. The third classifier algorithm 715 may determine whether a linear structure can be detected using the steepest-angled B-mode frames. As an example and not by way of limitation, the plurality of B-mode frames may include frames captured at −12, −6, 0, +6, and +12 degrees. In such an example, the third classifier algorithm 715 may consider the frames captured at −12 and +12 degrees. The third classifier algorithm 715 may determine whether the considered B-mode frames clearly depict an interventional instrument, as discussed above. If the third classifier algorithm 715 determines that an interventional instrument is present, for example, via detection of tissue warping or detection of linear structures in one or more B-mode frames, it may output a score indicating whether the interventional instrument is to the left or right, and send the output to voting algorithm 750. In particular embodiments, the third classifier algorithm 715 may be the same as the first classifier algorithm 740, as both are trained to detect tissue warping or linear structures in one or more frames.

In particular embodiments, voting algorithm 750 may receive the outputs from first classifier algorithm 740, second classifier algorithm 744, and third classifier algorithm 715, each of which provided an output value including determinations of whether an interventional instrument is present, and from which direction. In particular embodiments, voting algorithm 750 may determine a weighted average of the outputs from the classifier algorithms to determine the most likely direction the interventional instrument was placed, and the most suitable angle. In particular embodiments, voting algorithm 750 may itself have been trained to output certain values for direction and angle based on the specific inputs received from the classifier algorithms. In particular embodiments, voting algorithm 750 may compute the average value corresponding to direction of entry over a period of time, which may account for any false positives in the images over time. As an example and not by way of limitation, if voting algorithm 750 determines for 50 consecutive sets of ultrasound images that an interventional instrument is being inserted from the right, then for two sets of ultrasound images, the voting algorithm 750 determines that the interventional instrument is on the left, then for the following sets of ultrasound images the interventional instrument is detected on the right, voting algorithm 750 may determine that the two sets determined to be on the left was actually a false positive, and continue to capture needle frames of a right-side entry throughout this time period. In particular embodiments, voting algorithm 750 may determine from the classifier algorithms that no interventional instrument is present at the time, and determine that no needle frames are necessary. In particular embodiments, the determination that there is no interventional instrument may be determined only if a sufficient number of consecutive sets of ultrasound images do not show an interventional instrument, so that any false negatives may be smoothed out.

At step 755, voting algorithm 750 may adaptively control the signal path control (SPCTL) of the ultrasonic imaging system. The SPCTL may be used to update the frame sequencer of the ultrasonic imaging system in order to capture left or right needle frames 760 at the angles particularly suited for interventional instruments. In particular embodiments, based on the output of the voting algorithm 750, only one needle frame 760 may be necessary to provide a blended image. In particular embodiments, based on the output of the voting algorithm 750, the ultrasonic imaging system may determine that no needle frames are necessary in order to visualize the interventional instrument. As an example and not by way of limitation, voting algorithm 750 may determine that the steep B-mode frames used for the composite tissue frame (and the third classifier algorithm) are sufficient for linear structure detection.

At step 765, based on the needle frame 760 captured for visualization of the interventional instrument, the ultrasonic imaging system may determine whether a linear structure exists in the needle frame 760. The ultrasonic imaging system may subsequently create an enhanced linear structure 770, registered to the tissue frame. At step 780, the composite tissue frame 730 and the enhanced linear structure 770 are combined into a blended image 790, which may then be displayed.

Particular embodiments may repeat one or more steps disclosed in FIG. 7, where appropriate. Although this disclosure describes and illustrates particular steps of the method of FIG. 7 as occurring in a particular order, this disclosure contemplates any suitable steps of the method of FIG. 7 occurring in any suitable order. Moreover, although this disclosure describes and illustrates particular components, devices, or systems carrying out particular steps of the method of FIG. 7, this disclosure contemplates any suitable combination of any suitable components, devices, or systems carrying out any suitable steps of the method of FIG. 7.

In particular embodiments, the present invention utilizing always-on detection of interventional instruments, and automated left-right entry detection of the interventional instruments, may offer an advantage over previous needle entry detection systems by improving the frame rate at which the blended image can be created. As an example and not by way of limitation, by reducing the number of needle frames that must be captured during instrument visualization to one or zero frames (from three or more frames), less time is required to capture the needle frames for use in the blended frame, effectively increasing the frame rate of the ultrasound imaging. In particular embodiments, the frame rate of the blended images may be improved in direct proportion to the reduction in needle frames required. In particular embodiments, another advantage of the present invention may be an improved user experience in using the ultrasound imaging system, by not requiring the user to divert attention to specifying that (1) an interventional instrument will be used, and (2) which direction the instrument is being inserted from.

The subject matter and the operations described in this specification may be implemented in digital electronic circuitry, or in computer software, firmware, or hardware, including the structures disclosed in this specification and their structural equivalents, or in combinations of one or more of them. Embodiments of the subject matter described in this specification may be implemented as one or more computer programs, i.e., one or more modules of computer program instructions, encoded on computer storage medium for execution by, or to control the operation of, data processing apparatus.

A computer storage medium may be, or may be included in, a computer-readable storage device, a computer-readable storage substrate, a random or serial access memory array or device, or a combination of one or more of them. Moreover, while a computer storage medium is not a propagated signal, a computer storage medium may be a source or destination of computer program instructions encoded in an artificially-generated propagated signal. The computer storage medium also may be, or may be included in, one or more separate physical components or media (e.g., multiple CDs, disks, or other storage devices).

The term "processor" encompasses all kinds of apparatus, devices, and machines for processing data, including by way of example a programmable processor, a computer, a system on a chip, or multiple ones, or combinations, of the foregoing. The apparatus may include special purpose logic circuitry, e.g., an FPGA (field programmable gate array) or an ASIC (application-specific integrated circuit). The apparatus also may include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment may realize various different computing model infrastructures, such as web services, distributed computing and grid computing infrastructures.

A computer program (also known as a program, software, software application, script, or code) may be written in any form of programming language, including compiled or interpreted languages, declarative or procedural languages, and it may be deployed in any form, including as a stand-alone program or as a module, component, subroutine, object, or other unit suitable for use in a computing environment. A computer program may, but need not, correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform actions by operating on input data and generating output. The processes and logic flows may also be performed by, and apparatus can also be implemented as, special purpose logic circuitry, e.g., an FPGA (field programmable gate array) or an ASIC (application-specific integrated circuit).

Processors suitable for the execution of a computer program may include, by way of example and not by way of limitation, both general and special purpose microprocessors. Devices suitable for storing computer program instructions and data may include all forms of non-volatile memory, media and memory devices, including by way of example but not by way of limitation, semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in, special purpose logic circuitry.

From the foregoing, it may be appreciated that specific embodiments of the invention have been described herein for purposes of illustration, but that various modifications may be made without deviating from the scope of the invention. Accordingly, the invention is not limited except as by the appended claims.

What is claimed is:

1. An ultrasound imaging system comprising an image processor configured to:
   create a composite tissue frame from ultrasound image frames wherein the ultrasound image frames are captured at a plurality of first steer angles;
   determine that an interventional instrument is present in the ultrasound image frames based on one or more classifier algorithms trained to detect interventional instruments based at least in part on a detection of tissue warping within:
   one or more of the ultrasound image frames; or
   the composite tissue frame;
   determine that an additional image frame is required to depict the interventional instrument;
   determine a second steer angle of the additional image frame and capture the additional image frame at the second steer angle, wherein the second steer angle is greater than each of the plurality of first steer angles;
   based on the additional image frame, determine a linear structure corresponding to the interventional instrument; and
   compound the linear structure depicted in the additional image frame with the composite tissue frame to create a blended image frame depicting the interventional instrument.

2. The ultrasound imaging system of claim 1, wherein the ultrasound image frames comprise:
   at least one ultrasound image frame captured at a steer angle of 0 degrees; and
   at least one additional ultrasound image frame captured at a steer angle between −15 and +15 degrees.

3. The ultrasound imaging system of claim 1, wherein the one or more classifier algorithms comprises a classifier algorithm trained to determine that an interventional instrument is present based on movement detected in a difference frame generated from the composite tissue frame and a prior tissue frame captured by the ultrasound imaging system.

4. The ultrasound imaging system of claim 1, wherein a plurality of outputs from the one or more classifier algorithms are combined to determine that an interventional instrument is present.

5. The ultrasound imaging system of claim 4, wherein the combination of the plurality of outputs comprises a weighted average of the plurality of outputs.

6. The ultrasound imaging system of claim 1, wherein the one or more classifier algorithms comprise a classifier algorithm based on a neural network.

7. The ultrasound imaging system of claim 1, wherein the one or more classifier algorithms comprise a classifier algorithm trained to identify a left or right entry of an interventional instrument.

8. The ultrasound imaging system of claim 1, wherein the processor is further configured to determine, from a plurality of needle frames, which of the needle frames most prominently shows the presence of the interventional instrument, and designate that needle frame as the additional image frame.

9. The ultrasound imaging system of claim 1, wherein the processor is further configured to determine that an ultrasound probe is curved and perform a scan conversion.

10. The ultrasound imaging system of claim 1, wherein the one or more classifier algorithms comprise a classifier algorithm trained to determine that an interventional instrument is present, without relying upon a needle visualization frame, and by:
    classifying images depicting non-cyclic temporal changes in anatomy as potentially containing an interventional instrument; and
    disregarding changes in anatomy resulting from cyclic temporal changes.

11. The ultrasound imaging system of claim 10, wherein:
    the one or more classifier algorithms comprise a classifier algorithm trained to determine that an interventional instrument is present by:
      comparing the composite tissue frame with a second composite tissue frame;
      generating a frame difference based on the comparison, the frame difference representing the non-cyclic temporal change;
      detecting the tissue warping based on the frame difference;
      determining, based on the detection of tissue warping:
        the presence of the interventional instrument; and
        a location of the interventional instrument;
    the composite tissue frame and the second composite tissue frame comprise composite tissue frames that are at least one of:
      consecutive frames in time;
      separated by a predetermined amount of time; or
      separated by a predetermined quantity of frames; and
    selection of the composite tissue frame and the second composite tissue frame is determined:
      automatically, by the ultrasound imaging system based on an image-capture setting; or
      by a user input.

12. One or more computer-readable non-transitory storage media embodying software operable when executed by one or more computing devices of an ultrasound imaging system to:
    create a composite tissue frame from ultrasound image frames wherein the ultrasound image frames are captured at a plurality of first steer angles;
    determine that an interventional instrument is present in the ultrasound image frames based on one or more classifier algorithms trained to detect interventional instruments based at least in part on a detection of tissue warping within:
    one or more of the ultrasound image frames; or
    the composite tissue frame;
    determine whether an additional image frame is required to depict the interventional instrument;

determine a second steer angle of the additional image frame and capture the additional image frame at the second steer angle, wherein the second steer angle is greater than each of the plurality of first steer angles;

based on the additional image frame, determine a linear structure corresponding to the interventional instrument; and compound the linear structure depicted in the additional image frame with the composite tissue frame to create a blended image frame depicting the interventional instrument.

13. The computer-readable non-transitory media of claim 12, wherein the ultrasound image frames comprise:
at least one ultrasound image frame captured at a steer angle of 0 degrees; and
at least one additional ultrasound image frame captured at a steer angle between −15 and +15 degrees.

14. The computer-readable non-transitory media of claim 12, wherein the one or more classifier algorithms comprises a classifier algorithm trained to determine that an interventional instrument is present based on movement detected in a difference frame generated from the composite tissue frame and a prior tissue frame captured by the ultrasound imaging system.

15. The computer-readable non-transitory media of claim 12, wherein a plurality of outputs from the one or more classifier algorithms are combined to determine that an interventional instrument is present.

16. The computer-readable non-transitory media of claim 15, wherein the combination of the plurality of outputs comprises a weighted average of the plurality of outputs.

17. The computer readable transitory media of claim 12, wherein the one or more classifier algorithms comprise a classifier algorithm based on a neural network.

18. The computer readable transitory media of claim 12, wherein the one or more classifier algorithms comprise a classifier algorithm trained to identify a left or right entry of an interventional instrument.

19. The computer-readable non-transitory storage media of claim 12, wherein the software is further operable when executed by one or more computing devices of an ultrasound system to determine, from a plurality of needle frames, which of the needle frames most prominently shows the presence of the interventional instrument, and designate that needle frame as the additional image frame.

20. The computer-readable non-transitory storage media of claim 12, wherein the software is further operable when executed by one or more computing devices of an ultrasound system to determine that an ultrasound probe is curved and perform a scan conversion.

21. The computer-readable non-transitory storage media of claim 12, wherein the one or more classifier algorithms comprise a classifier algorithm trained to determine that an interventional instrument is present, without relying upon a needle visualization frame, and by:
classifying images depicting non-cyclic temporal changes in anatomy as potentially containing an interventional instrument; and
disregarding changes in anatomy resulting from cyclic temporal changes.

22. The computer-readable non-transitory storage media of claim 12, wherein:
the one or more classifier algorithms comprise a classifier algorithm trained to determine that an interventional instrument is present by:
comparing the composite tissue frame with a second composite tissue frame;
generating a frame difference based on the comparison, the frame difference representing the non-cyclic temporal change;
detecting the tissue warping based on the frame difference;
determining, based on the detection of tissue warping:
the presence of the interventional instrument; and
a location of the interventional instrument;
the composite tissue frame and the second composite tissue frame comprise composite tissue frames that are at least one of:
consecutive frames in time;
separated by a predetermined amount of time; or
separated by a predetermined quantity of frames; and
selection of the composite tissue frame and the second composite tissue frame is determined:
automatically, by the ultrasound imaging system based on an image-capture setting; or
by a user input.

* * * * *